(12) United States Patent  
Akiba (10) Patent No.: US 6,638,214 B2
(45) Date of Patent: Oct. 28, 2003

(54) OBSERVATION WINDOW WASHING DEVICE OF ENDOSCOPE

(75) Inventor: Haruo Akiba, Ibaraki (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/088,529

(22) PCT Filed: Jul. 31, 2001

(86) PCT No.: PCT/JP01/06599
§ 371 (c)(1),
(2), (4) Date: Apr. 2, 2002

(87) PCT Pub. No.: WO02/11607
PCT Pub. Date: Feb. 14, 2002

(65) Prior Publication Data
US 2002/0151768 A1 Oct. 17, 2002

(30) Foreign Application Priority Data
Aug. 2, 2000 (JP) ......... 2000-234068

(51) Int. Cl.[7] .................................. A61B 1/12
(52) U.S. Cl. ................. 600/157; 600/156; 600/158
(58) Field of Search ................. 600/114, 121, 600/123, 156, 157, 158

(56) References Cited

U.S. PATENT DOCUMENTS

| 5,207,213 | A | * | 5/1993 | Auhll et al. ............... 600/104 |
| 5,685,823 | A | * | 11/1997 | Ito et al. ................... 600/127 |
| 5,944,654 | A | * | 8/1999 | Crawford .................. 600/157 |
| 5,993,380 | A | * | 11/1999 | Yabe et al. ................ 600/121 |
| 6,095,971 | A | * | 8/2000 | Takahashi ................. 600/159 |
| 6,409,657 | B1 | * | 6/2002 | Kawano .................... 600/157 |

| 2002/0026097 | A1 | * | 2/2002 | Akiba ..................... 600/157 |

FOREIGN PATENT DOCUMENTS

| JP | 10-127578 | 5/1998 |
| JP | 11-99122 | 4/1999 |
| JP | 11-137516 | 5/1999 |
| JP | 11-192202 | 7/1999 |
| JP | 11-276424 | 10/1999 |
| JP | 2000-166855 | 6/2000 |
| JP | 2000-262462 | 9/2000 |

* cited by examiner

Primary Examiner—Linda C. M. Dvorak
Assistant Examiner—Kenneth G Schopfer
(74) Attorney, Agent, or Firm—Oblon, Spivak, McClelland, Maier & Neustadt, P.C.

(57) ABSTRACT

A notched void portion 29 is provided in a rigid casing block 20 of a rigid tip end section 2c of an endoscopic insertion instrument 2. For spurting a cleaning fluid toward an observation window 11, a cleaning supply passage is constituted by a cleaner nozzle 13, a connector pipe 27 and a flexible tube 26. A cleaner nozzle 13 is partly fitted in the notched void portion 29 which is formed in the rigid casing block 20. The connector pipe 27 is formed in a staggered shape having an angularly bent intermediate pipe section 27c between straight and parallel front and rear pipe sections 27a and 27b. The straight front pipe section 27a is at least partly fitted in the rigid casing block 20 and its fore distal end portion is fitted in the cleaner nozzle 13 over a predetermined length. On the other hand, the flexible tube is fitted on a rear end portion of the straight rear pipe section 27b the position of which is offset radially inward relative to the straight front pipe section 27a by the angularly bent intermediate pipe section 27c to avoid interference with biopsy channel 24, light guides 24 and wiring cable 17 which are threaded through a foremost angle ring 40 of an angle section 2b of the insertion instrument 2.

4 Claims, 7 Drawing Sheets

OBSERVATION WINDOW WASHING DEVICE OF ENDOSCOPE

FIELD OF THE ART

This invention relates to a device for cleaning an endoscopic observation window which is provided at a distal end of an elongated insertion instrument of a medical endoscope, and more particularly to an endoscopic observation window cleaning device which is particularly suitable for application to a medical endoscope having a narrow insertion instrument of a reduced diameter for insertion into a body cavity.

BACKGROUND OF THE ART

Generally, endoscopes which are in use in medical fields are largely composed of a manipulating head assembly to be gripped and manipulated by an operator, an elongated insertion instrument extended out on the front side of the manipulating head assembly for insertion into a body cavity, and a universal cable led out from the manipulating head assembly for connecting same to a light source (or to a light source and a processor).

The insertion instrument is provided with at least an illumination window and an observation window on a distal end face. It is usually the case that the illumination window is provided either at one or two positions on the distal end face. A diffuser lens is fitted in each illumination window in front of a light emitting end of a light guide which is connected to a light source. On the other hand, an optical objective lens system is fitted in the observation window, and a solid-state image sensor device is located at the focus of the objective lens system. Further, an outlet of a biopsy channel is opened in the distal end face of the insertion instrument. Therefore, when a diseased portion is spotted as a result of an endoscopic examination, forceps or other biopsy or surgical instruments are passed through the biopsy channel and projected into the body cavity to make a necessary treatment. Further, the endoscope is provided with the so-called observation window cleaning device thereby to spurt a cleaning fluid toward the observation window in case it is contaminated with body fluids or the like. Normally, the observation window cleaning device is provided on the distal end face of the insertion instrument, and largely composed of a jet nozzle for spurting a cleaning fluid, a mixture of a cleaning liquid and compressed air, toward the observation window, and a cleaning fluid supply passage which supplies the cleaning fluid to the jet nozzle. The cleaning fluid supply passage is extended through the insertion instrument and into the universal cable via the manipulating head assembly.

A rigid tip end section which is attached to the fore distal end of the insertion instrument is largely constituted by a rigid support structure and an insulating cap which is fitted on the distal end of the insertion instrument. From the standpoint of strength and machinability, the rigid support structure is formed of metallic material and encased in the insulating cap in such a way as to preclude its exposure to the outside. The rigid support structure is provided with a predetermined number of axial perforations or bores in which the above-mentioned light guide, optical objective lens system, biopsy channel and jet nozzle are to be fitted.

For the endoscopic insertion instrument which is introduced into a body cavity, it is desirable to be as narrow as possible or as small as possible in outside diameter in order to lessen the pains on the side of patients. Therefore, various component parts to be fitted in the endoscopic insertion instrument should be compact and small in size as long as intended functions of these parts are available, and various attempts have been made in this regard, including layout and positional relations of various component parts within the insertion instrument. As a consequence, the thickness of insertion instruments of recently developed endoscopes has been reduced almost to a limit. Nevertheless, there is a strong demand for further reductions in diameter of endoscopic insertion instruments. In addition, to cope with sophistication of endoscopic examinations and treatments or to cope with increases in functions which are required of an endoscope, there has been a tendency toward incorporating an increased number of component parts into an endoscopic insertion instrument, for example, in order to provide two biopsy channels on one endoscopic insertion instrument or to add a lens drive mechanism to an optical objective lens system in an observation window for a zooming function. Accordingly, it is important to position an increased number of required component parts rationally within a limited space of a narrow endoscopic insertion instrument without necessitating to increase its outside diameter.

DISCLOSURE OF THE INVENTION

In view of the foregoing situations, it is an object of the present invention to provide an endoscopic observation window cleaning device which permits to reduce the outside diameter of a narrow endoscopic insertion instrument further to an extremely small size.

It is a more particular object of the present invention to provide an endoscopic observation window cleaning device having a cleaner nozzle fitted in position at a distal end of a narrow endoscopic insertion instrument in such a way as to permit reduction of the outside diameter of the insertion instrument further to an extremely small size.

In order to achieve the above-stated objectives, according to the present invention, there is provided an endoscopic observation window cleaning device for an endoscope having an elongated insertion instrument extended out from a manipulating head assembly, the insertion instrument having an angle section and a rigid tip end section successively connected to a fore end of an elongated flexible body, the rigid tip end section having a rigid casing block connected to a foremost one of angle rings of the angle section by fitting engagement therewith and sheathed in an insulating cap in distal end portions including a distal end face with at least openings for an observation window and an illumination window axially in alignment with corresponding openings in the insulating cap, along with an opening for a cleaner nozzle connected to a cleaning fluid supply passage and arranged to spurt a cleaning fluid toward the observation window, the endoscopic observation window cleaning device comprising: a nozzle fitting portion being axially bored through the rigid casing block of the rigid tip end section and having a small diameter portion and a radially spread large diameter portion opened in the distal end face of the rigid casing block; a notched void portion being formed in the rigid casing block laterally on the outer side of the large diameter portion of the nozzle fitting portion in such a way as to form an outermost segment of the large diameter portion; and a cleaner nozzle fitted in the large diameter portion of the nozzle fitting portion to form a cleaning fluid supply passage along with a connector pipe fitted in the small diameter portion of the nozzle fitting portion and connected in the angle section to a flexible tube from a cleaning fluid supply source; the cleaner nozzle being fitted in the large diameter portion of the nozzle fitting portion and partly in the notched void portion in the rigid casing block; and the connector pipe being in a staggered shape having an angularly bent intermediate pipe section between straight and parallel front and rear pipe sections and the flexible tube being fitted on the rear pipe section of the connector pipe in the angle section at a position offset radially inward relative to the front pipe section and free of interference with other component parts threaded through the angle section.

The foremost one of angle rings which constitute the angle section of the insertion instrument is connected to the rigid casing block of the rigid tip end section. Other angle rings of the angle section are successively and pivotally connected to the foremost angle ring, and various component parts are threaded or fitted internally of the angle section. Therefore, there is little space in the angle section for the connector pipe of the cleaning fluid supply passage to be extended and to be connected to the flexible tube which constitutes a rear part of the cleaning fluid supply passage. Therefore, it is necessary and important to control the position of the connector pipe in the angle section accurately by way of the angularly bent pipe section because otherwise there will arise the problem of interference with other component parts in the angle section. For this purpose, an index mark is provided on a rear end face of the rigid casing block to indicate a direction in which the angularly bent intermediate section of the connector pipe is to be set. Further, a fore end portion of the connector pipe is fitted in the cleaner nozzle which is partly fitted in the notched void portion in the rigid casing block. The notched void portion is provided in the rigid casing block in such a way as to form an outer segment of a nozzle fitting portion, that is to say, to make an extra space for fitting the cleaner nozzle at the distal end of the endoscopic insertion instrument. Seal material is applied on and around outer periphery of the cleaner nozzle in the notched void portion to anchor same in position and to insure air tightness of the insertion instrument.

BEST MODE FOR CARRYING OUT THE INVENTION

Figure 1:
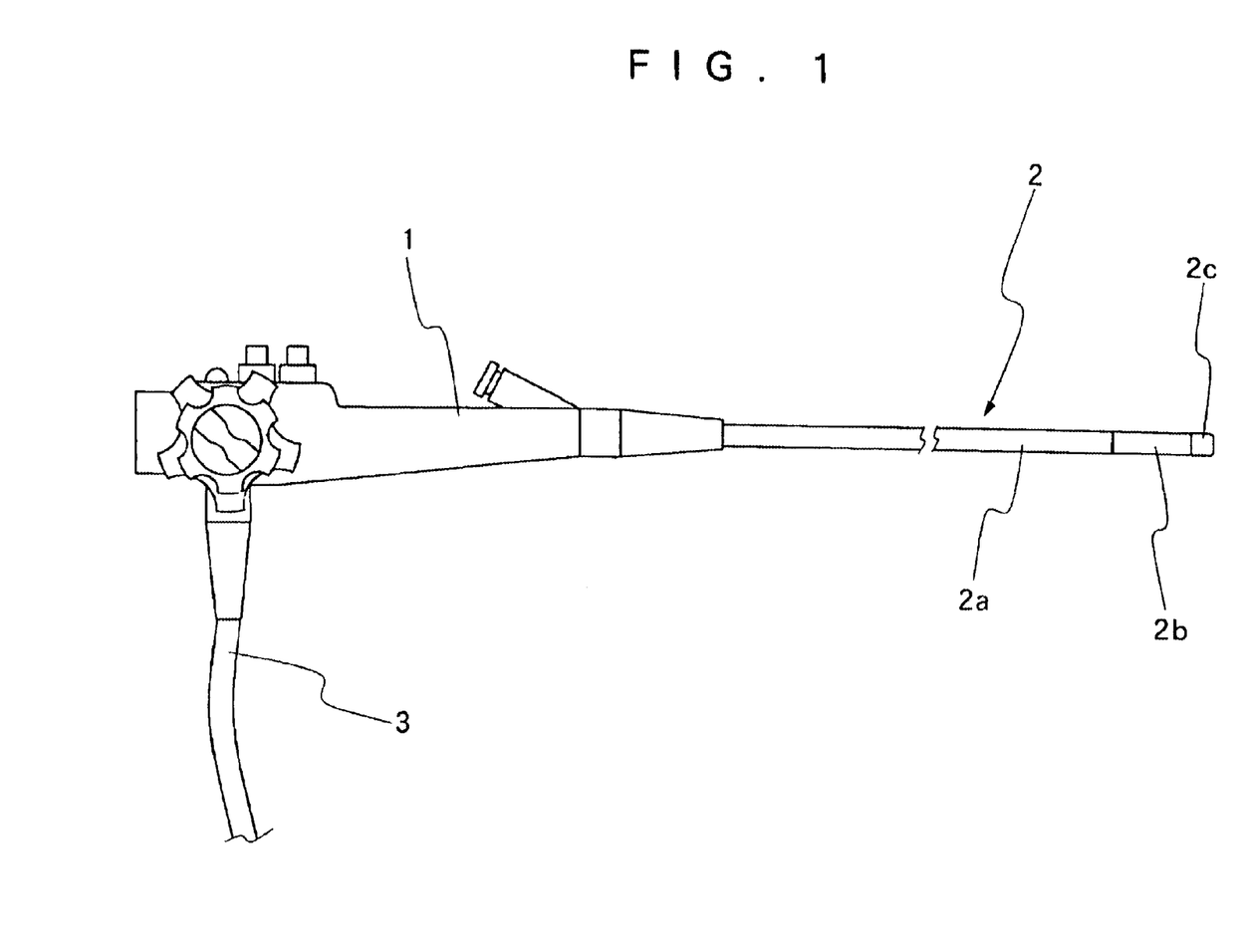
FIG. 1 is a schematic outer view of an endoscope as a whole, incorporating an embodiment according to the present invention.

Hereafter, the present invention is described more particularly by way of its preferred embodiments with reference to the accompanying drawings. Firstly, reference is had to FIG. 1 which shows general layout of an endoscope. In this figure, indicated at 1 is a manipulating head assembly, at 2 an insertion instrument and at 3 a universal cable of the endoscope. From a proximal end which is connected to the manipulating head assembly 1, the endoscopic insertion instrument 2 is successively composed of an elongated flexible body section 2a, an angle section 2b and a rigid tip end section 2c. The flexible body section 2a, which is in the form of a flexible tube structure, is flexibly bendable into arbitrary directions along curved or bent portions which may exist in a path of insertion into a body cavity. Therefore, a major part of the endoscopic insertion instrument 2 is constituted by the flexible body section 2a. The angle section 2b can be angularly turned into an upward, downward, rightward or leftward direction by remote control from the manipulating head assembly 1. Accordingly, the rigid tip end section 2c can be turned into a desired direction by bending the angle section 2b.

Figure 2:
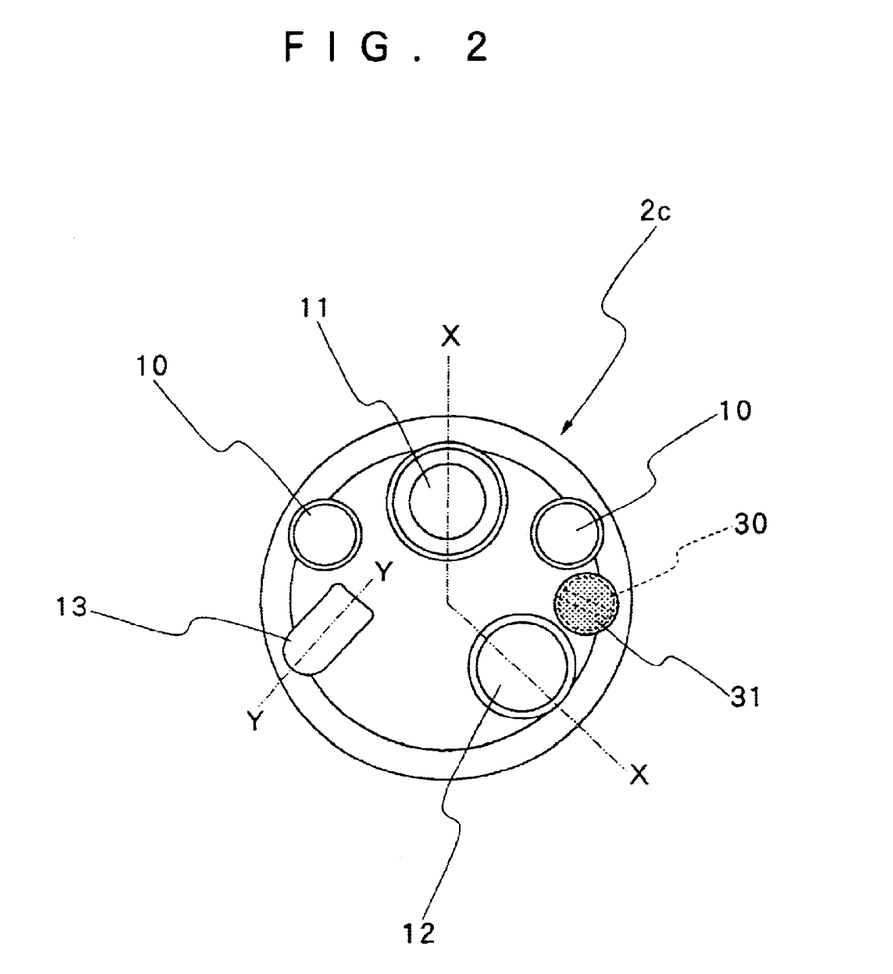
FIG. 2 is a schematic end view of an end face at the fore distal end of an insertion instrument of the endoscope.

Schematically shown in FIG. 2 is a distal end face of the rigid tip end section 2c of the insertion instrument 2. A couple of illumination windows 10 are provided on the distal end face of the rigid tip end section 2c (one or three illumination windows are provided in some cases), and an observation window 11 is located at an intermediate position between the two illumination windows 10. Largely opened under the observation window 11 is an outlet 12 of a biopsy channel. Further, a cleaner nozzle 13 is provided in the vicinity of the outlet 12 of the biopsy channel to spurt a wash fluid toward the observation window 11.

Figure 3:
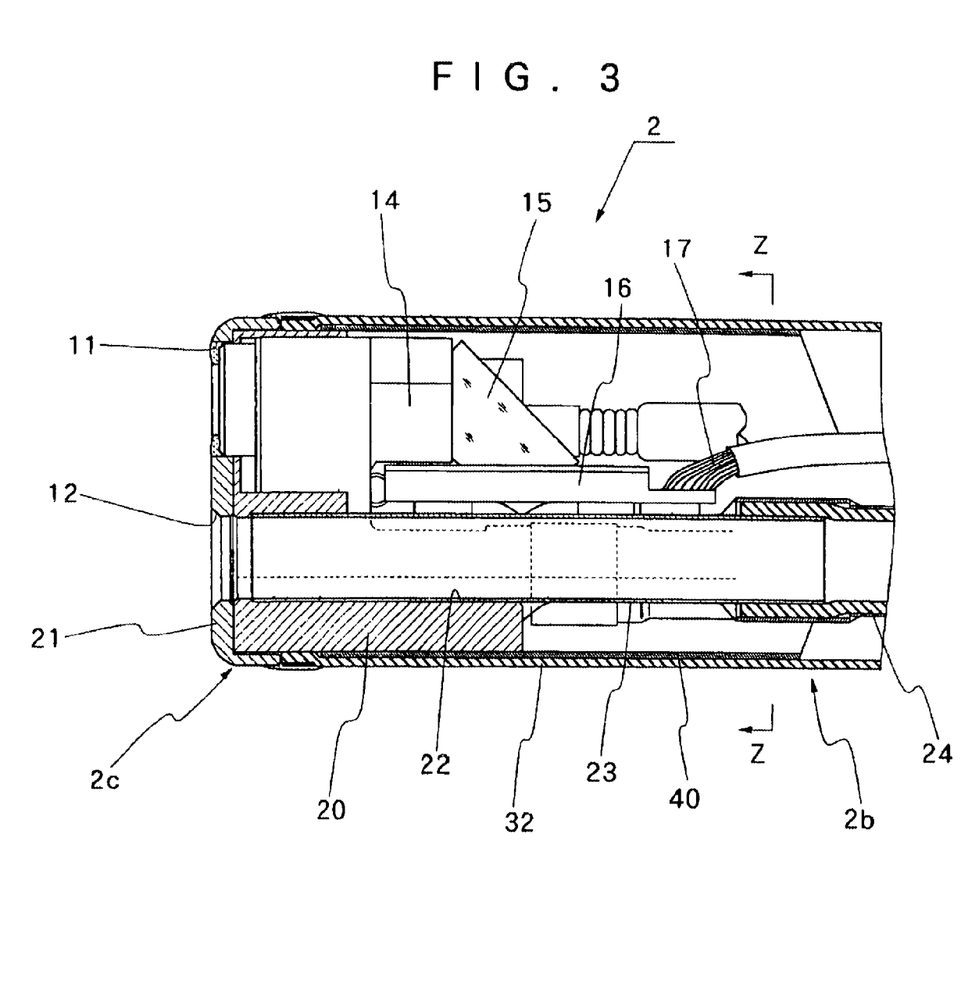
FIG. 3 is a schematic sectional view taken on line X—X of FIG. 2.

Although not shown in the drawings, a light diffuser lens is fitted in each illumination window 10 in front of a light emitting end of an illumination light guide. On the other hand, as shown in FIG. 3, a lens barrel 14 of an optical objective lens system is located behind the observation window 11. In the case of the particular example which is shown in the drawings, the objective lens system is provided with a prism 15 to turn a light path through 90 degrees to focus picture images on a solid-state image sensor device 16 which is mounted in a horizontal state, namely, which is located in a plane parallel with the longitudinal axis of the insertion instrument 2. Needless to say, the objective lens system can be arranged to focus picture images on a solid-state image sensor device which is located in a plane perpendicular to the longitudinal axis of the insertion instrument, without bending its light path. Indicated at 17 is a wiring cable which is connected to the image sensor device 16. The outlet 12 of biopsy channel is provided to protrude forceps or other instruments into a body cavity whenever necessary for a treatment. From the cleaner nozzle 13, a mixture of a cleaning liquid and compressed air is spurted toward the observation window 11 for cleaning same when contaminated with body fluids or the like. Namely, the cleaner nozzle 13 functions to spurt a cleaning fluid toward the observation window 11, and constitutes a fluid supply passage along with a connector pipe 27 and a flexible tube 26 which will be described hereinlater.

The rigid tip end section 2c is constituted by a rigid casing block 20 consisting of a metal block of substantially columnar shape, and an insulating cap 21 which is fitted on a distal end face of the rigid casing block 20. A number of axial bores are formed through the rigid casing block 20 for fitting the above-mentioned light guides, lens barrel of the objective lens system 14, biopsy channel and cleaner nozzle 13, in alignment or in communication with openings which are provided in the insulating cap 21 for the illumination windows, observation window and outlets of the biopsy channel and cleaning fluid passage, respectively.

Figure 4:
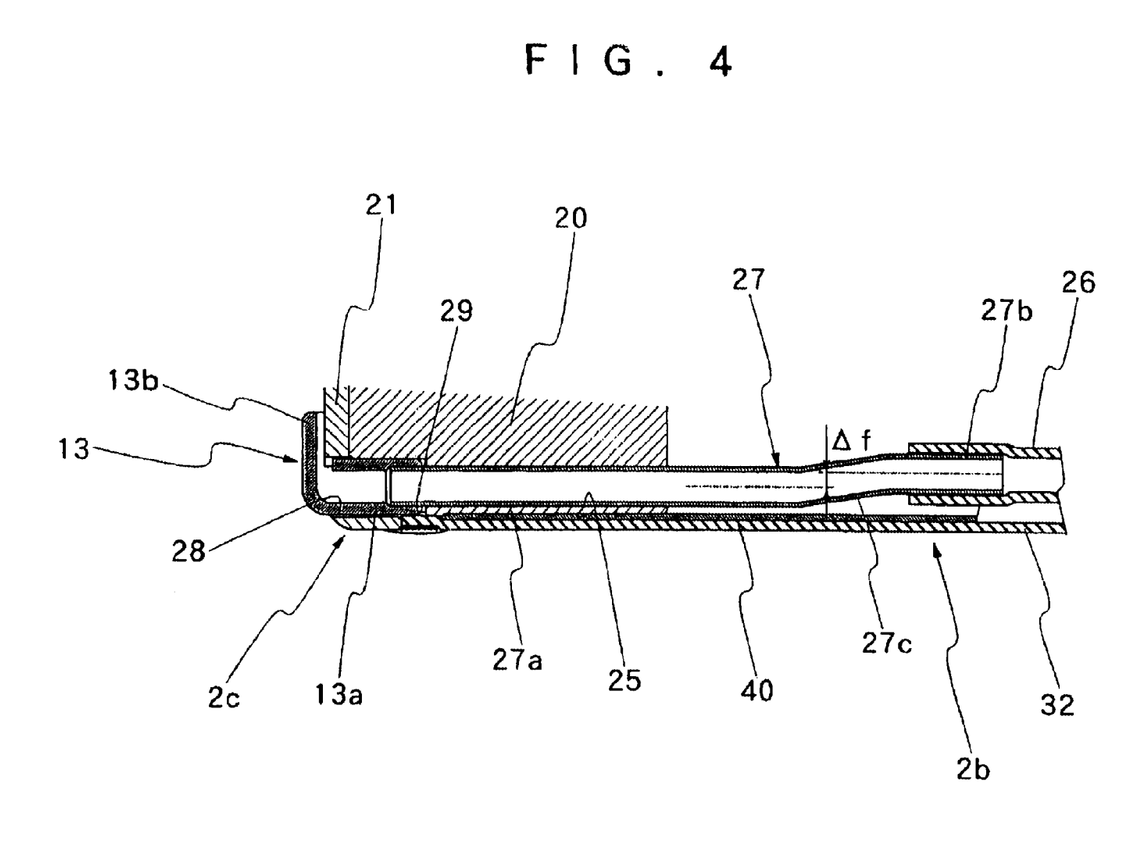
FIG. 4 is a schematic sectional view taken on line Y—Y of FIG. 2.

FIG. 3 shows the rigid tip end section 2c in a longitudinal section taken through the outlet 12 of the biopsy channel, while FIG. 4 shows the same in a longitudinal section taken through the cleaner nozzle 13. Indicated at 22 in FIG. 3 is a bore which is formed axially through the rigid casing block 20 to provide an instrument outlet passage 22. The instrument outlet passage 22 is bulged into a larger diameter at its base end for fitting a connector pipe 23 therein. In turn, a fore end portion of a biopsy channel 24 which is constituted by a flexible tube is fitted in the connector pipe 23.

As clear from FIG. 4, a nozzle fitting bore portion 25 is provided in the rigid casing block 20 of the rigid tip end section. Placed in the nozzle fitting bore portion 25 is a connector pipe 27 which is connected to a fore end of a flexible tube 26 of a cleaning fluid supply passage. In order to spurt a cleaning fluid, a mixture of a cleaning liquid and compressed air toward the observation window 11, the cleaner nozzle 13 is arranged to turn an axial flow of the cleaning fluid through 90 degrees. For this purpose, the cleaner nozzle 13 is composed of an axial tubular body portion 13a and a spout portion 13b which is turned through 90 degrees from the tubular body portion 13a and opened toward the observation window 11. In this instance, the spout portion 13b is extended along the outer surface of the insulating cap 21, while the axial body portion 13a is extended into an opening 28 which is provided in the insulating cap 21.

The nozzle fitting bore portion 25, mainly consisting of an axial bore which is formed in the rigid casing block 20, is not uniform in diameter but varied stepwise in the longitudinal direction. Namely, the nozzle fitting bore portion 25 is provided with a small diameter portion 25a on the side of its base end, and a large diameter portion 25b which is extended over a predetermined length from its fore distal end. The large diameter portion 25b of the nozzle fitting bore portion 25 is so positioned as to axially register and align with the outer periphery of the rigid casing block 20 on the outer side. Therefore, there is no wall of any thickness to cover an outermost segment of the large diameter portion 25b of the nozzle fitting bore portion 25. Namely, the rigid casing block 20 is provided with a notched void portion 29 of a predetermined width on the outer side of the large diameter portion 25b of the nozzle fitting bore portion 25, permitting to shift the position of the large diameter portion 25b in a radially outward direction by a distance corresponding to a thickness of a wall which would normally exist on the outer side of the large diameter portion 25b. The tubular body portion 13a of the cleaner nozzle 13 is fitted in the large diameter portion 25b of the nozzle fitting portion 25.

Figure 5:
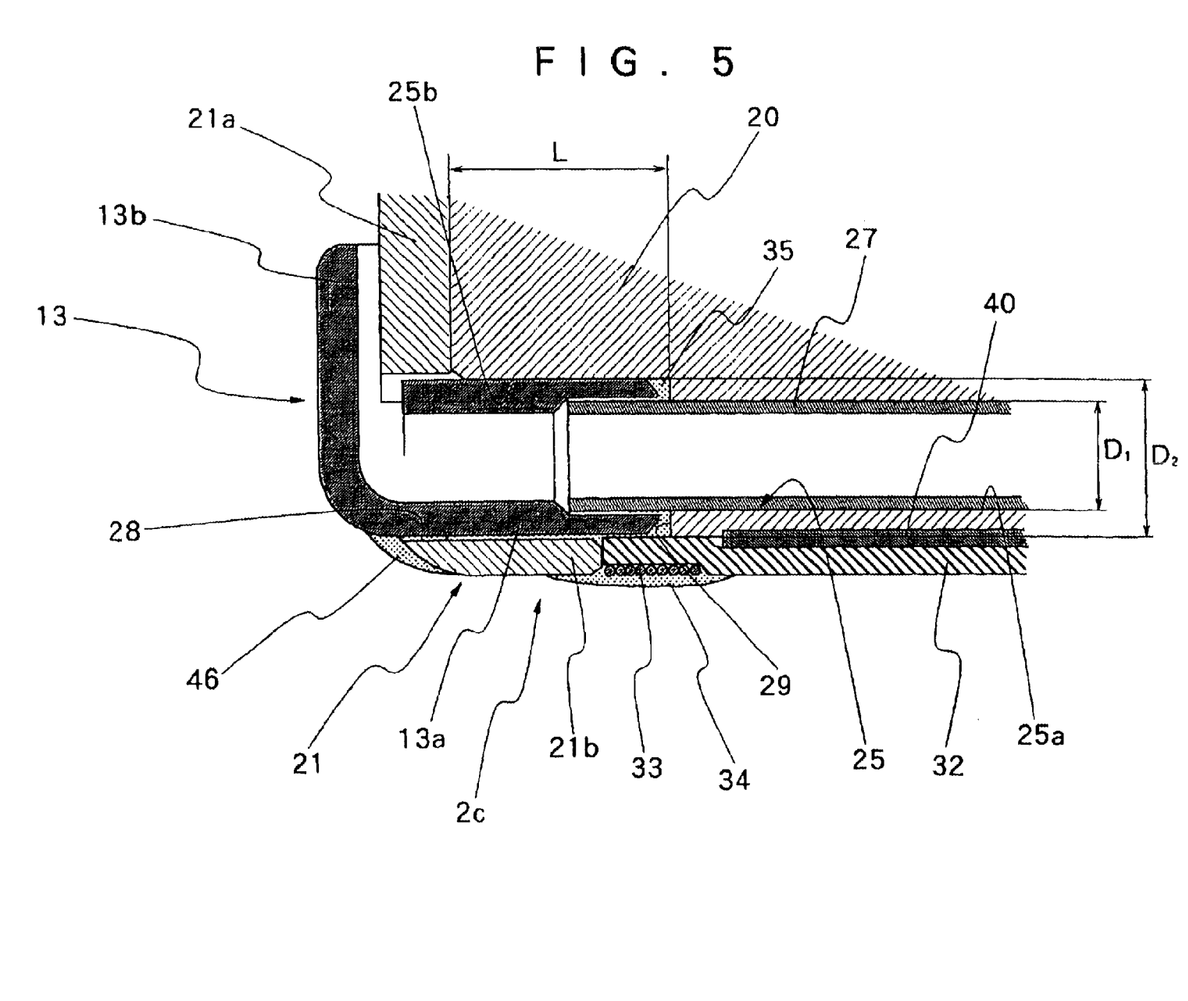
FIG. 5 is a schematic sectional view, showing on an enlarged scale major component parts which are shown in FIG. 4.

The small diameter portion 25a of the axial bore which constitutes the nozzle fitting portion 25 is formed in a minimum necessary diameter for fitting the connector pipe 27, while the large diameter portion 25b is formed in a suitable size for fitting the tubular body portion 13a of the cleaner nozzle 13. As seen in FIG. 5, the provision of the notched void portion 29 in the rigid casing block 20 permits to increase the inside diameter of the nozzle fitting portion 25 by utilizing the notched void portion 29 in the rigid casing block as part of the large diameter portion 25b for fitting the cleaner nozzle 13.

The rigid casing block 20 which is formed of a metallic material needs to be completely shielded in an electrically insulating member. Therefore, the insulating cap 21 is arranged to enshroud the rigid casing block 20 and constituted by a distal end face 21a and a circumferential portion 21b which is fitted on the circumference of the rigid casing block 20. The insulating cap 21 is securely fixed to the rigid casing block by means of a set screw 30 (see FIG. 2), which is covered under seal material 31 and thereby retained in an unexposed state. Proximal end of the circumferential portion 21b of the insulating cap 21 is joined with a fore end of an outer skin layer 32 of synthetic resin, rubber or other electrically insulating material, which is extended from the side of the angle section 2b and fixedly anchored in position by line wrapping 33. An adhesive 34 is applied across the meeting ends of the outer skin layer 32 and the insulating cap 21 and around the line wrapping 33 to fix the outer skin layer 32 and to hermetically seal the joint portion of the outer skin layer 32 and the insulating cap 21.

In this instance, as clear from FIG. 2, it is desirable to provide a certain degree of diametrical differential between the outside diameter of the rigid casing block 20 and the inside diameter of the circumferential portion 21b of the insulating cap 21 so that the insulating cap 21 is loosely fitted around the rigid casing block 20. With such a diametrical differential, it becomes easier to fit the insulating cap 21 on the rigid casing block 20 even if openings in the distal end face 21a are arranged to tightly and substantially hermetically fit on the illumination windows 10, the observation window 11 etc. In this instance, it is desirable to fill seal material in a gap space which may exists between the rigid casing block 20 and the insulating cap 21. However, there is no necessity for filling a gap space between the rigid casing block 20 and the insulating cap 21 completely with seal material because a hermetical seal is formed by the adhesive 34 which is applied around and across meeting ends of the outer skin layer 34 and the circumferential portion 21b of the insulating cap 21 as described hereinbefore.

The nozzle 13 which is projected on the outer side of the fore distal end of the rigid tip end section 2c is formed of a suitable material in electrically insulating properties, more specifically, formed of hard plastics or synthetic resin material. In this regard, the cleaner nozzle 13 needs to have a wall thickness markedly greater than the connector pipe 27 because plastic material is inferior to a metal pipe in strength, for example, a wall thickness several times as large as that of the connector pipe 27. Namely, as compared with the outside diameter of the tubular body portion 13a of the cleaner nozzle 13, the outside diameter of the connector pipe 27 which constitutes part of the cleaning fluid supply passage can be reduced to a sufficient degree for placement in the small diameter portion 25a of the nozzle fitting portion 25 in the rigid casing block 20.

On the other hand, the tubular body portion 13a of the cleaner nozzle 13 which is located at the fore distal end of the rigid casing block 20 is partly fitted in the latter and is relatively short in axial length. Taking these points into consideration, as shown particularly in FIG. 5, the nozzle fitting portion 25 on the rigid casing block 20 is provided with the large diameter portion 25b of a predetermined length L from its fore distal end, and a notched void portion 29 is provided in the rigid casing block 20 immediately on the outer side of the large diameter portion 25b to utilize the notched void portion as part of the large diameter portion in securing a sufficiently large diameter $D_2$ for fitting the cleaner nozzle 13 on the front side of the narrow small diameter portion 25a with a far smaller diameter $D_1$. Thus, the provision of the notched void portion 29 makes it possible to fit the cleaner nozzle 13 into a limited narrow space despite its large wall thickness as compared with the connector pipe 27, locating an outer lateral side of the tubular body portion 13a of the cleaner nozzle 13 substantially flush with the outer periphery of the rigid casing block 20 in the axial direction. In this manner, the shift of the cleaner nozzle fitting portion to a notched void portion which is provided at one lateral side of the rigid casing block 20 permits to reduce the outside diameter of the rigid casing block 20 as compared with a case in which the nozzle fitting portion is bored completely through and within the rigid casing block 20. Namely, it becomes possible to reduce the diameter of the endoscopic insertion instrument 2 itself. Besides, the shift of the cleaner nozzle 13 to one lateral side of the insertion instrument contributes to make an extra room or space in or in the vicinity of central areas of the rigid casing block 20, which will give a greater degree of freedom in laying out other component parts to be incorporated into the insertion instrument 2.

The tubular body 13a of the cleaner nozzle 13 which is fitted in the large diameter portion 25b of the nozzle fitting bore 25 is also partly fitted in the notched void portion 29 to have its outer end substantially flush with the outer periphery of the rigid casing block 20, and enshrouded in the circumferential portion 21b of the insulating cap 21 along with the rigid casing block 20. The connector pipe 27 which is fitted in the small diameter portion 25a is extended rearward of the proximal end of the rigid casing block and into the angle section 2b and fitted in a flexible tube 26. The angle section 2b is provided with angle rings 40 as structural units. As well known in the art, the angle section 2b is constituted by a plural number of angle rings 40 which are pivotally connected in series alternately by way of vertical and horizontal joints, and is angularly bendable in four directions by pulling paired operating wires either in a forward or backward direction. Therefore, if the connector pipe 27 is extended into the angle section 2b in a straight form, there will be almost no gap space between the connector pipe 27 and the angle ring 40 which will permit to fit the flexible tube 26 on the connector pipe 27, and there may arise a problem of interference with the angle section operating wires or other component parts which are threaded through the angle section 2b.

In order to avoid the problems as mentioned above, the connector pipe 27 is bent into a staggered shape having an angularly bent intermediate pipe section 27c between straight front and rear pipe sections 27a and 27b to offset the rear section 27b radially inward of the front section 27a in parallel relation with the latter. The straight front section 27a is placed in the nozzle fitting portion 25 in the rigid casing block 20, while the straight rear section 27b is fitted in the flexible tube 26. Thus, relative to the straight front section 27a, the straight rear section 27b is offset radially inward by a distance Δf (see FIG. 4). The rear section 27b of the connector pipe 27 is spaced apart from the inner periphery of the angle ring 40 to make a room or a gap space for fitting the flexible tube 26 thereon.

Figure 6:
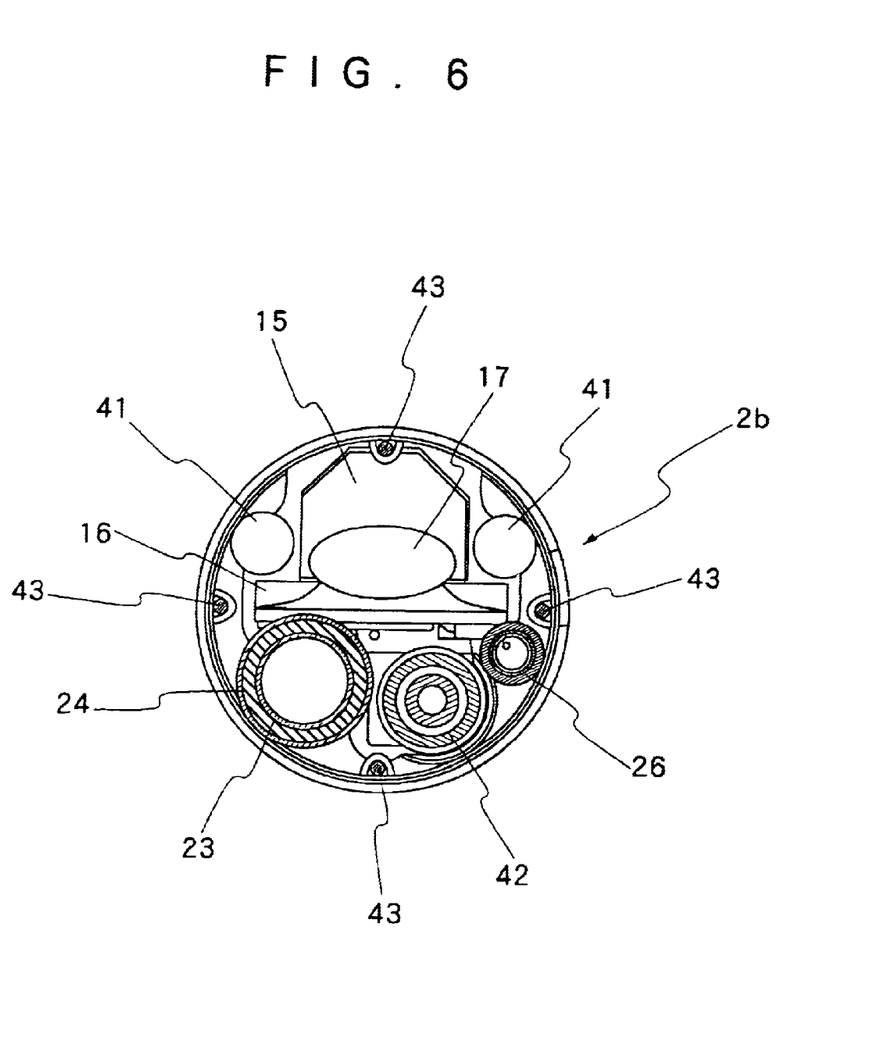
FIG. 6 is a schematic sectional view taken on line Z—Z of FIG. 3.

In the case of the particular embodiment shown, the biopsy channel 24, light guides 41 and wiring cable 17 from the image sensor means 16 are passed through the angle section 2b of the insertion instrument 2 as seen in FIG. 6, along with a control cable 42 serving as a lens drive means for the optical objective lens system, and four operating wires 43 for bending the angle section 2b, i.e., a pair of upper and lower operating wires and a pair of right and left operating wires, for bending the angle section 2b by remote control from the manipulating head assembly. Therefore, the flexible tube 26 which constitutes a fluid supply passage should be located not only in a position which is spaced from the inner periphery of the angle ring 40 but also in a position precisely intermediate between the control cable 42 and the operating wires 43. This means that, at the time of fitting the connector pipe 27, it is necessary and important to control the direction of the bent section 27c of the connector pipe 27 correctly.

Figure 7:
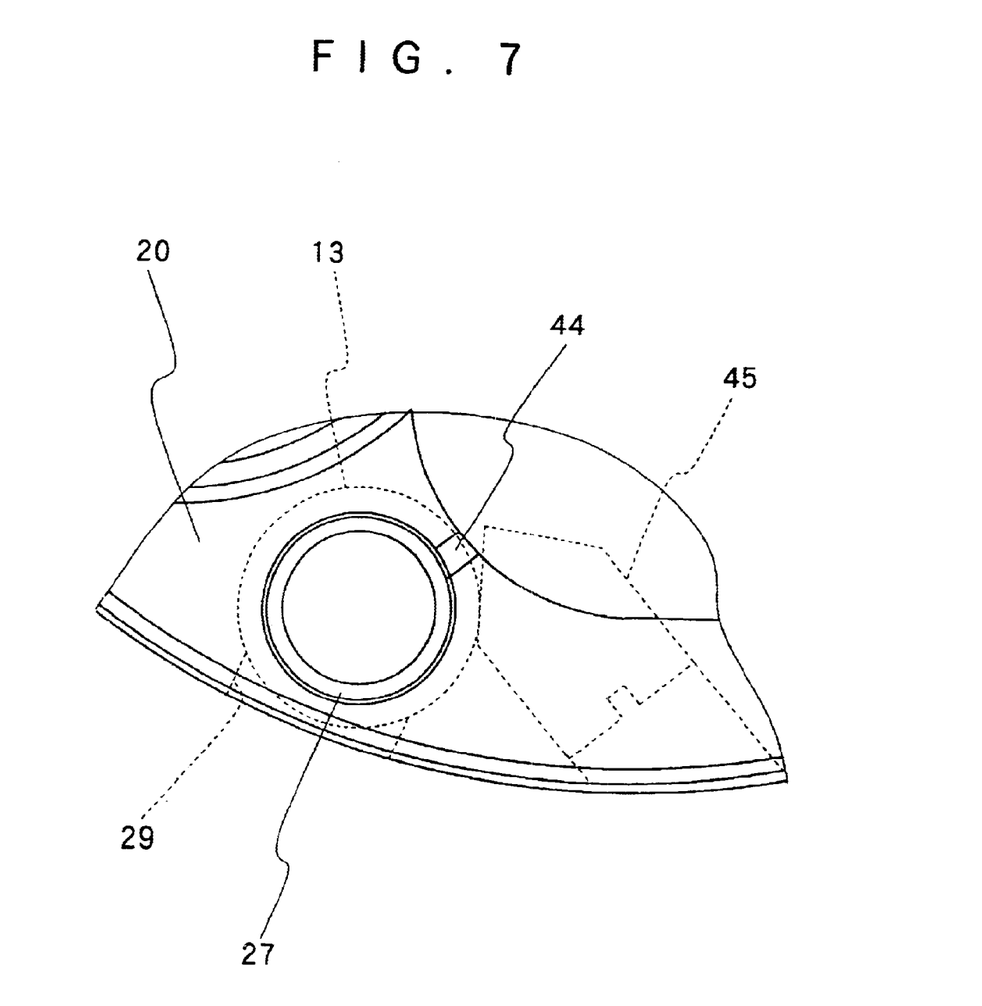
FIG. 7 is a schematic view of a base end portion of a rigid tip end section of the insertion instrument.

As shown in FIG. 7, in order to correctly control the direction of the angularly bent section 27c of the connector pipe 27, an index mark 44 is provided on a rear end face of the rigid casing block 20 to indicate the direction in which the angularly bent pipe section 2c should be set. The index mark 44 may be a color mark but, from the standpoint of stability and durability as a directional index, it is preferable to form a notch, groove, rib or ridge-like protuberance on the rear end face of the rigid casing block. Thus, by turning the connector pipe 27 into the direction of the index mark 44 after placing the straight front pipe section 27a in the nozzle fitting portion 25, the straight rear pipe section 27b of the connector pipe can be set in position within the angle section 2b, free of interferences with other component parts which are passed through the angle section 2b. Accordingly, it becomes possible to make adjustments so that the flexible tube 26 can be easily fitted on the straight pipe section 27b. In FIG. 7, indicated at 45 is a set screw which fixes the cleaner nozzle 13 in position.

In this instance, after placing the connector pipe 27 into the tubular body portion 13a of the cleaner nozzle 13 over a predetermined fitting length, seal material 35 is is applied around the rear end of the tubular body 13a to fill in the gap space between these two parts. The applied seal material 35 contributes to anchor the cleaner nozzle 13 in position, to improve air tightness of the insertion instrument 2 and to preclude irregular variations in outside diameter. Besides, since a fore end portion of the connector pipe 27 is placed in the tubular body portion 13a of the cleaner nozzle 13 over a substantial length, there is no possibilities of the applied seal material 35 getting into the cleaning fluid supply passage within the connector pipe 27 and the cleaner nozzle 13. Therefore, if desired, the inside diameter of the cleaner nozzle 13 may be appreciably differentiated from the outside diameter of the connector pipe 27 for the purpose of facilitating their fitting engagement. Further, an adhesive 46 is applied around the outer periphery of a transitional nozzle portion between the tubular body portion 13a and the spout portion 13b of the cleaner nozzle 13 thereby to securely anchor the cleaner nozzle 13 in position and at the same time to insure air tightness of the insertion instrument 2.

In the foregoing preferred embodiment, it has been described that the whole cleaner nozzle 13 is formed of a synthetic resin material or plastics. However, it may be formed of a metallic material as long as it is electrically insulated from the rigid casing block 20. In the case of a metallic cleaner nozzle, it is desirable to fit an insulating sleeve on the outer periphery of the tubular body portion of the cleaner nozzle. In such a case, however, the outside of the cleaner nozzle is inevitably increased by addition of an insulating sleeve. Nevertheless, the outside diameter of an endoscopic insertion instrument can be reduced to a minimum size by locating the insulating sleeve within a notched void portion 29 which is formed in a rigid casing block of a rigid tip end section of the insertion instrument.

What is claimed is:

1. An endoscope and an endoscopic observation window cleaning device for the endoscope having an elongated insertion instrument extended out from a manipulating head assembly, said insertion instrument having an angle section and a rigid tip end section successively connected to a fore end of an elongated flexible body, said rigid tip end section having a rigid casing block connected to a foremost one of angle rings of said angle section by fitting engagement therewith and sheathed in an insulating cap in distal end portions including a distal end face with at least openings for observation and illumination windows axially in alignment with corresponding openings in said insulating cap, along with an opening for a cleaner nozzle connected to a cleaning fluid supply passage and arranged to spurt a cleaning fluid toward said observation window, said endoscopic observation window cleaning device comprising:

a nozzle fitting portion being axially bored through said rigid casing block of said rigid tip end section and having a small diameter portion and a radially spread large diameter portion opened in said distal end face of said rigid casing block;

a notched void portion being formed in said rigid casing block laterally on the outer side of said large diameter portion of said nozzle fitting portion in such a way as to form an outermost segment of said large diameter portion; and a cleaner nozzle fitted in said large diameter portion of said nozzle fitting portion to form a cleaning fluid supply passage along with a connector pipe fitted in said small diameter portion of said nozzle fitting portion and connected in said angle section to a flexible tube from a cleaning fluid supply source;

said cleaner nozzle being fitted in said large diameter portion of said nozzle fitting portion and partly in said notched void portion in said rigid casing block; and said connector pipe being in a staggered shape having an angularly bent intermediate pipe section between straight and parallel front and rear pipe sections and said flexible tube being fitted on said rear pipe section of said connector pipe in said angle section at a position offset radially inward relative to said front pipe section and free of interference with other component parts threaded through said angle section.

2. An endoscope and an endoscopic observation window cleaning device as defined in claim 1, wherein said large diameter portion of said nozzle fitting portion is located to have said outer segment substantially flush with outer periphery of said rigid casing block, and said notched void portion is formed to have a radial width containing an outer segment of both said large diameter portion and said rigid casing block.

3. An endoscope and an endoscopic observation window cleaning device as defined in claim 1, wherein said rigid casing block is provided with an index mark on a rear end face thereof to indicate a direction in which said angularly bent intermediate pipe section is to be set within said angle section of said insertion instrument.

4. An endoscope and an endoscopic observation window cleaning device as defined in claim 1, wherein a seal material is applied around outer peripheral portions in said notched void portion of said rigid casing block.

* * * * *